United States Patent [19]

Guggenheim

[11] Patent Number: 4,714,780

[45] Date of Patent: Dec. 22, 1987

[54] METHOD FOR MAKING TETRAHYDROXYDIPHENYLSULFIDE AND PRODUCT OBTAINED THEREFROM

[75] Inventor: Thomas L. Guggenheim, Glenville, N.Y.

[73] Assignee: General Electric Company, Schenectady, N.Y.

[21] Appl. No.: 824,915

[22] Filed: Feb. 3, 1986

[51] Int. Cl.$^4$ ............................................. C07C 149/30
[52] U.S. Cl. .................................... 564/430; 568/44; 568/48
[58] Field of Search ..................... 568/48, 44; 564/430

[56] References Cited

U.S. PATENT DOCUMENTS

| | | | |
|---|---|---|---|
| 3,060,121 | 10/1962 | Orloff et al. | 568/48 |
| 4,115,590 | 9/1978 | Lerner | 514/712 |
| 4,380,671 | 4/1983 | Yamaguchi et al. | 568/48 |

FOREIGN PATENT DOCUMENTS 2031422A 4/1980 United Kingdom .

OTHER PUBLICATIONS

Hiroshi Kato, "Tetrahydroxydiphenyl Sulfide", Chemical Abstracts 88, #88:50470r (1978), p. 511.

"Prepn. of 2,2'-thio-bisphenol Derivs.", Derwent Pub. Ltd., Central Patents Index 83, #39, A+:Polymer Applications #J8 3042866-B (1983).

"Thiobis-phenol(s) & Resorcinol(s) Prodn.", Derwent Pub. Ltd., Central Patents Index, Week 8402, AE: Polymer+General Chemistry #FR 2527-603-A (1983).

Akihiro Yamaguchi et al., "Bis-(4-substituted Phenol)-Sulfides", Chemical Abstracts 93, #93:149974y (1980), p. 692.

Akihiro Yamaguchi et al, "Preparation of 2,2'-bis(-4-substituted-phenol Sulfides", Chemical Abstracts 94, #94:83765t (1981) p. 691.

Primary Examiner—Mary E. Ceperley
Attorney, Agent, or Firm—William A. Teoli; James C. Davis, Jr.; James Magee, Jr.

[57] ABSTRACT

Thiobisphenols, such as 2,2-bis[2,2-bis(4-hydroxyphenyl)propane]-sulfide are provided by effecting reaction between a dihydric phenol such as bisphenol-A and sulfur dichloride in the presence of an effective amount of a Lewis acid catalyst and organic solvent.

4 Claims, No Drawings

METHOD FOR MAKING TETRAHYDROXYDIPHENYLSULFIDE AND PRODUCT OBTAINED THEREFROM

BACKGROUND OF THE INVENTION

Thiobisphenol derivatives, such as 2,2'-bis(4-substituted phenol)sulfides, have been recognized as useful in such applications as light stabilizers, polyolefin modifiers, lubricant additives, or intermediates for such products, as shown by UK Pat. No. 2,031,422. Certain tetrahydroxydiphenylsulfides can be prepared by reacting resorcinol and sulfur dichloride in ether as taught by Japanese Pat. No. 7785,129. Experience has shown, however, that when certain bisphenols, such as bisphenol-A or phenols of the formula

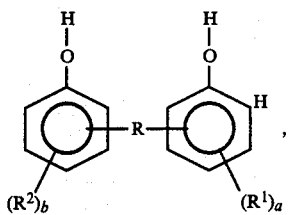

are reacted with sulfur dichloride in the presence of an organic solvent, oligomeric phenylsulfides can be formed in favor of the desired tetrahydroxydiphenylsulfide, where R is a $C_{(1-20)}$ divalent organo radical selected from the class consisting of $C_{(1-8)}$ alkylene radicals, $C_{(6-14)}$ arylene radicals or substituted $C_{(6-14)}$ arylene radicals, —O—, —S—,

—OR$^4$O—, —SR$^4$S—
and —C$_y$H$_{2y}$ radicals, where y is an integer equal to 1 to 5 inclusive, $R^1$ and $R^2$ are members selected from the class consisting of $C_{(1-8)}$ alkyl radicals, $C_{(1-8)}$ alkoxy radicals, $C_{(6-13)}$ aryloxy radicals, and $R^3$S— radicals, $R^3$ is a $C_{(1-13)}$ monovalent hydrocarbon radical, $R^4$ is a $C_{(6-14)}$ arylene radical, a is a whole number equal to 0–3 inclusive and b is a whole number equal to 0–4 inclusive.

The present invention is based on my discovery that optimum yields of tetrahydroxydiphenylsulfide of the formula

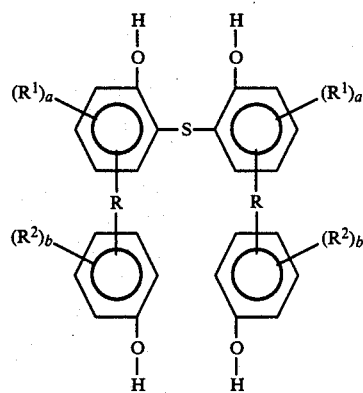

where R, $R^1$, and $R^2$, a and b are as prevously defined, can be formed by effecting reaction between at least five moles of bisphenol of Formula 1, per mole of sulfur dichloride, in the presence of Lewis acid catalyst and an inert organic solvent.

STATEMENT OF THE INVENTION

There is provided by the present invention, a method for making a tetrahydroxydiphenylsulfide of Formula 2 which comprises, (1) effecting reaction under substantially anhydrous conditions between at least five moles, and preferably 5 to 10 moles, of bisphenol of Formula 1, per mole of sulfur dichloride, in the presence of an effective amount of a Lewis acid catalyst and an inert organic solvent, and (2) recovering the tetrahydroxydiphenylsulfide from the mixture of (1).

Radicals which are included within R of Formula 1 and 2 are, for example, $C_{(1-8)}$ alkylene radicals, such as methylene, dimethylene, trimethylene, tetramethylene; $C_{(6-14)}$ arylene radicals such as phenylene, tolylene, xylylene, naphthylene; substituted arylene radicals such as chlorophenylene, nitrophenylene, ethoxyphenylene, divalent radicals such as CH$_3$N=, C$_6$H$_5$N=, oxyalkyleneoxy, thioalkylenethio,

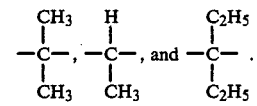

There are included within $R^1$ and $R^2$ the same or different $C_{(1-8)}$ alkyl radicals, such as methyl, ethyl, propyl, butyl, pentyl, $C_{(1-8)}$ oxyalkyl radicals such as methoxy, ethoxy, butoxy, oxy $C_{(6-13)}$ aryl radicals, such as oxyphenyl, oxytolyl, oxyxylyl, thiomethyl, thiophenyl.

Some of the tetrahydroxydiphenylsulfides which are included within Formula 2 are, for example,

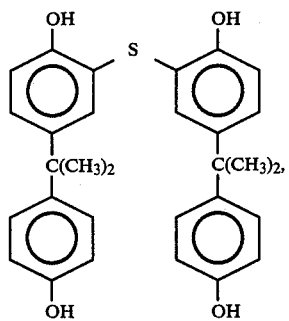

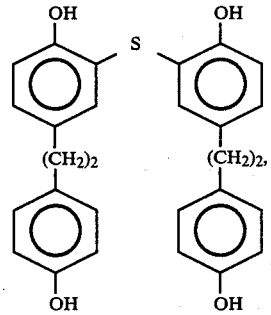

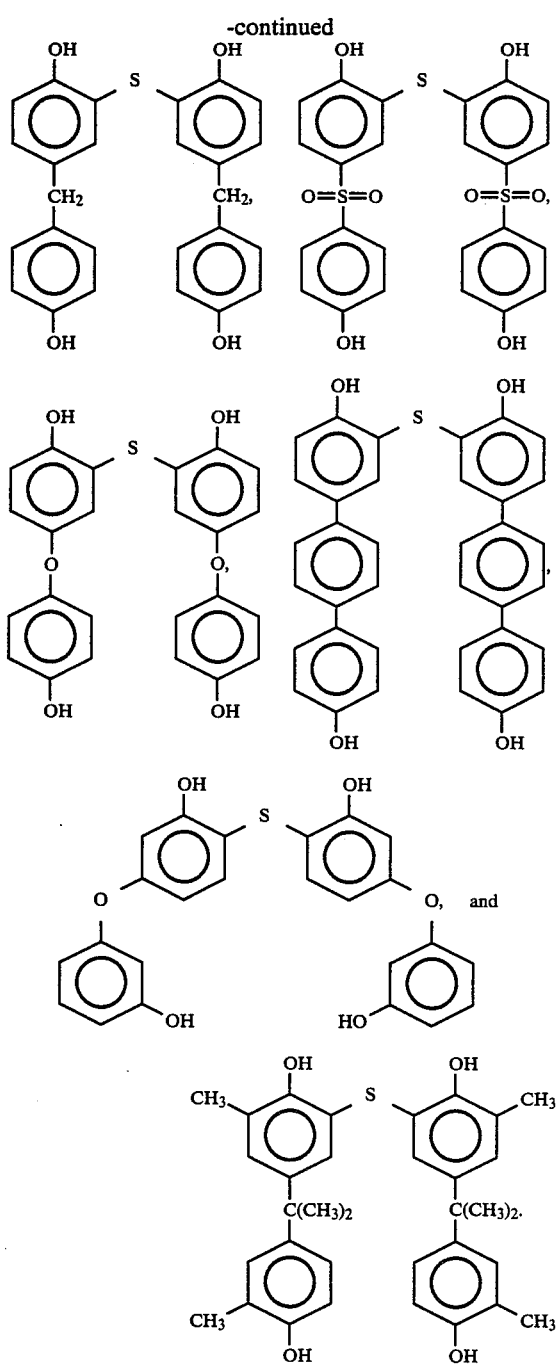

In the practice of the invention, reaction is effected between the bisphenol, such as the phenol of Formula 1, and sulfur dichloride in the presence of a Friedel-Crafts catalyst and an inert organic solvent. Suitable Friedel-Crafts catalysts are, for example, zinc chloride, zinc iodide, zinc bromide, tin chloride, titanium tetrachloride, aluminum trichloride, boron trichloride, methyl aluminum dichloride, boron trifluoride, galium tribromide, antimony pentafluoride, and iron trichloride.

An effective amount of Friedel-Crafts catalyst is that amount which provides from about 0.5% to 1.5% by weight of Friedel-Crafts catalyst based on the weight of the reaction mixture.

Inert organic solvents which can be used in the practice of the present invention are, for example, diethylether, methylene chloride, hexane, toluene, benzene carbon tetrachloride, and chloroform.

Reaction between the bisphenol and the sulfurdichloride can be conducted at temperatures in the range of from 0° C. to 25° C. and preferably from 1° to 5° C. It has been found that optimum results are obtained when the present invention is practiced under substantially anhydrous conditions and under an inert atmosphere such as nitrogen or a noble gas.

The following examples are given by way of illustration and not by way of limitation. All parts are by weight unless otherwise indicated.

EXAMPLE 1

There was added drop-wise over a 10-minute period 0.103 grams (1.0 millimole) of sulfurdichloride to a solution of 1.13 grams (4.96 millimoles) of bisphenol-A, 0.05 gram (0.4 millimole) and zinc chloride and 30 ml of diethylether under a nitrogen atmosphere. The reaction mixture was stirred for 1.5 hours at 0° C. A clear red solution was obtained which was allowed to warm to room temperature. There was added 0.3515 gram of an internal standard, 2,2'-dihydroxydiphenylsulfone.

The ether was removed from the resulting red solution under reduced pressure and a thick oil was obtained. Medium pressure liquid chromatography of the oil on a 450 mm length (47 mm I.D.) Michel-Miller silica gel (230–400 mesh) column using 25% ethylacetate/hexane as an eluent gave three major products of high purity. There was obtained a 60% yield of a white crystalline solid having a melting point of 75°–79° C. Based on method of preparation and analysis such as IR(KBR) 3280, 2940, 1580, 1470, 1210, 1170, 820 cm; 13C nmr and mass spectrum for $C_{30}H_{30}O_4S$ calculated 486.1865, the product was 2,2'-thiobis(4-[1-methyl-1-(4-hydroxyphenyl)ethyl]-phenol.

There is added 0.05 to 0.1 part of the above tetrahydroxyphenylsulfide to 100 parts of a lubricating oil consisting of approximately 18–26% by weight of straight paraffin 8, 43–74% of alkylated naphthenes and the balance asphaltic substances. The resulting composition has improved resistance to oxidation.

While the above example is directed to only a few of the very many variables involved in the practice of the method of the present invention, it should be understood that the present invention is directed to the use of a much broader variety of bisphenols of Formula 1 as well as the organic solvents and Lewis acid catalyst used in the practice of such method.

What is claimed and sought to be protected by Letters Patent of the United States is as follows:

1. A method for making a tetrahydroxydiphenylsulfide of the formula,

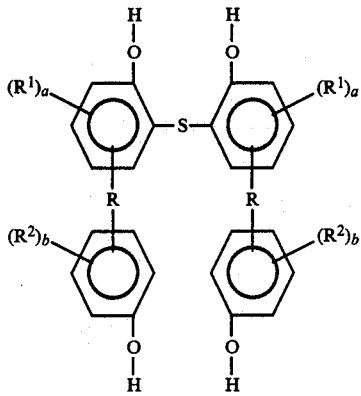

by (1) effecting reaction under substantially anhydrous conditions between at least five moles of bisphenol of the formula,

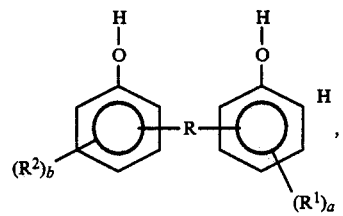

per mole of sulfur dichloride, in the presence of an effective amount of a Lewis acid catalyst and an inert organic solvent, and (2) recovering the tetrahydroxydiphenylsulfide from the mixture of (1).

where R is a $C_{(1-20)}$ divalent organo radical selected from the group consisting of $C_{(1-8)}$ alkylene radicals, $C_{(6-13)}$ arylene radicals, or chloro, nitro, alkoxy or alkyl substituted $C_{(6-13)}$ arylene radicals, —O—, —S—,

—OR⁴O—, and —SR⁴S— radicals, $R^1$ and $R^2$ are members selected from the group consisting of $C_{(1-8)}$ alkyl radicals, $C_{(1-8)}$ alkoxy radicals, $C_{(6-13)}$ aryloxy radicals, and $R^3S$— radicals, $R^3$ is methyl or phenyl, $R^4$ is a $C_{(6-14)}$ arylene radical, a is a whole number equal to 0 to 3 inclusive and b is a whole number equal to 0 to 4 inclusive.

2. A method in accordance with claim 1, where the bisphenol is bisphenol-A.

3. A method in accordance with claim 1, where the Lewis acid catalyst is zinc chloride.

4. 2,2-bis[2,2-bis(4-hydroxyphenyl)propane]sulfide.

* * * * *